(12) United States Patent
Bullens et al.

(10) Patent No.: US 8,052,610 B2
(45) Date of Patent: Nov. 8, 2011

(54) EVENT REGISTRATION FOR AUTOMATIC THRESHOLD SETTING

(75) Inventors: Roland W. M. Bullens, Maastricht (NL); Roger Kessels, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 211 days.

(21) Appl. No.: 11/617,063

(22) Filed: Dec. 28, 2006

(65) Prior Publication Data
US 2008/0161701 A1 Jul. 3, 2008

(51) Int. Cl.
*A61B 5/05* (2006.01)
*A61B 5/02* (2006.01)

(52) U.S. Cl. ........................ 600/481; 600/547

(58) Field of Classification Search .................. 600/484, 600/481, 547
See application file for complete search history.

(56) References Cited

U.S. PATENT DOCUMENTS

| | | | |
|---|---|---|---|
| 5,354,319 A | 10/1994 | Wyborny et al. | |
| 5,987,352 A | 11/1999 | Klein et al. | |
| 6,104,949 A | 8/2000 | Pitts Crick et al. | |
| 6,250,309 B1 | 6/2001 | Krichen et al. | |
| 6,442,433 B1 | 8/2002 | Linberg | |
| 6,480,745 B2 | 11/2002 | Nelson | |
| 6,482,154 B1 | 11/2002 | Haubrich et al. | |
| 6,522,915 B1 | 2/2003 | Ceballos et al. | |
| 6,574,511 B2 | 6/2003 | Lee | |
| 6,599,250 B2 | 7/2003 | Webb et al. | |
| 2002/0052539 A1* | 5/2002 | Haller et al. | 600/300 |
| 2003/0074029 A1* | 4/2003 | Deno et al. | 607/23 |
| 2004/0122488 A1* | 6/2004 | Mazar et al. | 607/60 |
| 2004/0127792 A1* | 7/2004 | Siejko et al. | 600/439 |
| 2006/0041280 A1 | 2/2006 | Stahmann et al. | |
| 2006/0167497 A1* | 7/2006 | Armstrong et al. | 607/2 |
| 2006/0281980 A1* | 12/2006 | Randlov et al. | 600/301 |
| 2006/0293609 A1* | 12/2006 | Stahmann et al. | 600/547 |

* cited by examiner

*Primary Examiner* — Patricia Mallari
*Assistant Examiner* — Christian Jang
(74) *Attorney, Agent, or Firm* — Reed A. Duthler; Stephen W. Bauer

(57) ABSTRACT

An implantable medical device includes a sensor for sensing a first signal in a patient, detection circuitry for receiving the first signal, determining a parameter therefrom, and detecting a first event in response to the parameter. The device further includes control circuitry configured to receive a second signal corresponding to a second event and to determine a threshold from the stored parameter in response to receiving the second event signal. The detection circuitry detects the first event in response to the parameter crossing the determined threshold.

14 Claims, 4 Drawing Sheets

EVENT REGISTRATION FOR AUTOMATIC THRESHOLD SETTING

TECHNICAL FIELD

The invention relates generally to implantable medical devices and, in particular, to a device and method for automatically setting a threshold for detecting a physiological event.

BACKGROUND

Implantable medical devices are available for monitoring physiological signals of a patient. Physiological signals may be analyzed by the device for automatically detecting an adverse physiological condition or event. The physiological monitoring may be used by the device for controlling automatic delivery of a therapy, such as an electrical stimulation therapy or a drug therapy. The medical device may be provided with a patient alarm for notifying the patient of the presence of the detected physiological event or condition. The patient may then take appropriate action, such as seeking medical attention, as previously advised by a clinician. Typically a threshold value is defined, which when crossed by a monitored physiological parameter triggers the patient alarm. The threshold for triggering an alarm may be set to a nominal value or a value derived from clinical data relating to a selected patient population. The threshold may not be individualized for a particular patient, potentially resulting in the triggering of false alarms. Such false alarms are inconvenient both to the patient and the treating physician. Accordingly, a method and apparatus are needed for setting an appropriate threshold for individual patients for detecting a physiological condition and triggering a patient alarm.

DETAILED DESCRIPTION

Figure 1:
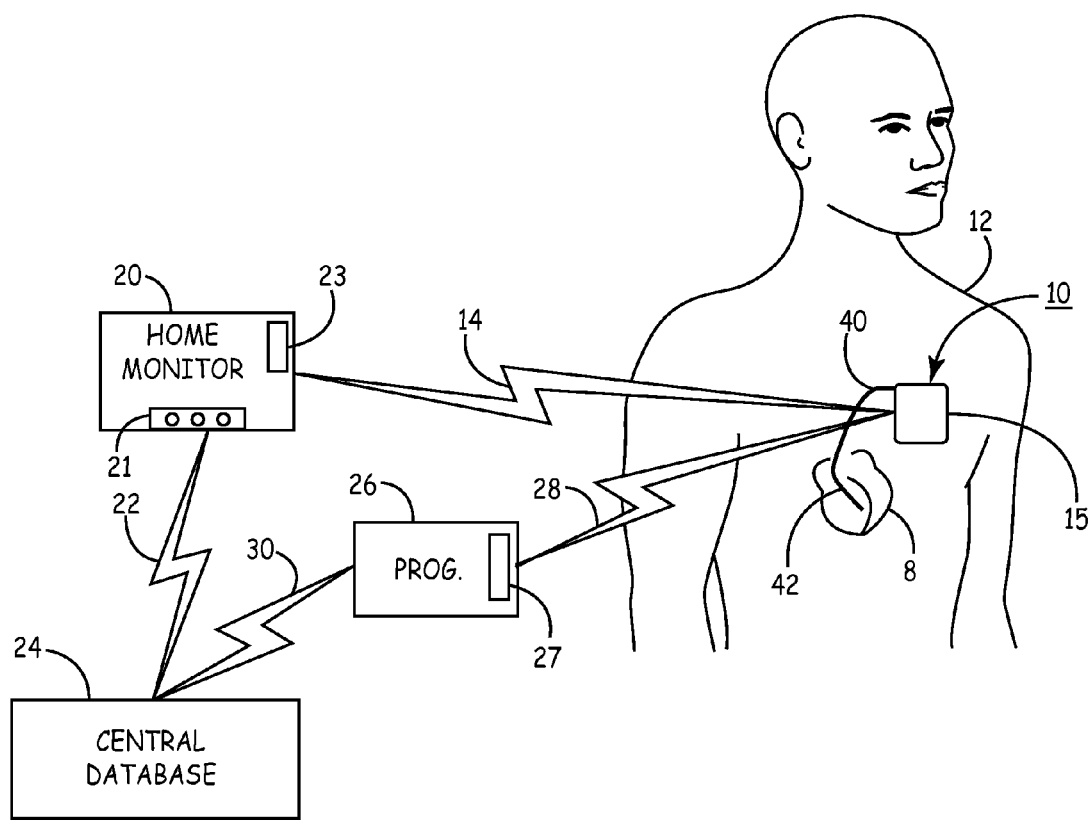
FIG. 1 illustrates an implantable medical device (IMD) system.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 illustrates an implantable medical device (IMD) system. IMD 10 is shown implanted in a patient 12. The simplified illustration of IMD 10 may represent a variety of IMDs such as a cardiac pacemaker, implantable cardioverter defibrillator, hemodynamic monitor, ECG recorder, or a drug delivery device. In alternative embodiments, an IMD may be implemented as an insulin monitor or pump, or a neuromuscular stimulator. IMD 10 may be coupled to one or more fluid delivery catheters or electrical leads 40. Lead 40 is used for carrying electrodes or physiological sensors used for monitoring one or more physiological signals and delivering electrical stimulation therapies to the patient's heart 8. IMD 10 may alternatively be embodied as a leadless device wherein sensors or electrodes are incorporated in or on the housing of IMD 10. Examples of leadless monitoring devices are generally disclosed in U.S. Pat. No. 6,522,915 issued to Ceballos et al., and U.S. Pat. No. 5,987,352 issued to Klein et al, both of which patents are incorporated herein by reference in their entirety.

Lead 40 is a ventricular lead including a coil electrode 42. Coil electrode 42 may be used in conjunction with IMD housing 15 for delivering cardioversion/defibrillation shocks to a patient. Lead 40 may also be provided with a tip electrode and a ring electrode for sensing cardiac signals and delivering cardiac pacing pulses. In one embodiment of the invention, coil electrode 42 is used in conjunction with IMD housing 15 to measure thoracic impedance for fluid monitoring. In patients suffering from congestive heart failure, an increase in pulmonary fluid congestion will result in a decrease in thoracic impedance. Monitoring of thoracic impedance over time allows a trend of worsening or improving edema to be tracked. Lead 40 is shown positioned in the right ventricle, however a ventricular lead may alternatively be positioned in operative relation to the left ventricle, for example in a cardiac vein via the coronary sinus.

In other embodiments lead 40 or other additional leads may be provided including other physiological sensors such blood pressure sensors, blood chemistry sensors, temperature sensors, oxygen sensors, flow sensors, wall motion sensors or the like. Furthermore, while IMD 10 is shown as a cardiac device coupled to the patient's heart 8 via lead 40, various embodiments of the invention may include other types of implantable medical devices that are enabled for monitoring a physiological signal for detecting a condition or event associated with a change in the monitored signal.

IMD 10 is provided with an antenna and associated circuitry, as will be described below, for establishing a communication link 14 with external telemetry circuitry 23 included in home monitor 20 and/or a communication link 28 with external telemetry circuitry 27 included in physician programmer 26. Home monitor 20 may include a user interface 21 that allows patient 12 or other caregiver to transmit commands or signals to IMD 10 using home monitor 20. Home monitor may be used by patient 12 or another caregiver to send a signal to IMD 10 indicating the occurrence of a clinical event. For example, by depressing a button on user interface 21, a signal may be transmitted from home monitor 20 to IMD 10 via telemetry link 14 indicating a serious clinical event has occurred. Among the types of events that may be indicated to IMD 10 are fainting, shortness of breath, and angina. As will be further described herein, IMD 10 determines a patient alarm threshold for a monitored physiological parameter in response to receiving the external signal. IMD 10 will trigger a patient alarm in response to the monitored parameter crossing the threshold. Home monitor 20 may be enabled to generate a patient alarm in response to receiving a signal from IMD 10 corresponding to a threshold crossing. A patient alarm may be provided as a visual display and/or audible sounds.

Home monitor 20 may be configured to receive data from IMD 10 for transmission to a central database 24 to enable remote monitoring of patient 12. In some embodiments, home monitor 20 may be enabled to program an operating mode or control parameters used by IMD 10.

IMD 10 is further enabled for bidirectional communication with a physician programmer 26 via telemetry link 28. Physician programmer 26 is generally located in a health care facility, such as a clinic or hospital, for use by medical personnel and is typically enabled for full programming and interrogation functions. Physician programmer 26 may also be used for transmitting an event signal to IMD 10 for triggering a threshold determination. For example, a clinician may use programmer 26 to indicate any of the events listed previously as well as hospitalization of the patient for symptoms relating to a monitored physiological parameter.

The event signal may include time and date information that is entered manually by a user to allow a user to send an event signal after the actual event. For example, if the patient or a caregiver forgets to transmit an event signal to the IMD 10 at the time of the event, the patient or caregiver may send the event signal at a later time including time and date information relating to the actual or approximate time of the event. Such time and date information may include ranges of times and/or days when the exact time of the event is unknown.

Home monitor 20 and/or programmer 26 may optionally be adapted to communicate with a central database 24 to allow transfer of data received from IMD 10 to the central database 24. A central database may be an Internet-based or other networked database used for remote patient monitoring. Home monitor 20 may transfer data via a communication link 22, which may be established via the Internet, a local area network, a wide area network, a telecommunications network or other appropriate communications network and may be a wireless communication link. Likewise, programmer 26 may receive data from IMD 10 and transfer the data to central database 24 using a communication link 30. Examples of remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

In remote patient monitoring systems, central database 24 may be used for detecting an event automatically and transmitting an event signal to the IMD 10 for triggering a threshold determination. For example, if a patient implanted with IMD 10 is admitted to a hospital, long-distance telemetry between IMD 10 and programmer 20 located in the hospital may be established such that programmer 20 is "aware" that the patient having IMD 10 has been hospitalized. Upon establishing communication with IMD 10, programmer 20 may transmit an event signal to IMD 10 triggering a threshold determination by IMD 10. Programmer 20 may transmit patient data to central database 24 indicating the patient has been hospitalized, in which case either programmer 20 or central database 24 may respond by initiating transmission of an event signal to IMD 10, triggering an automatic threshold determination.

Figure 2:
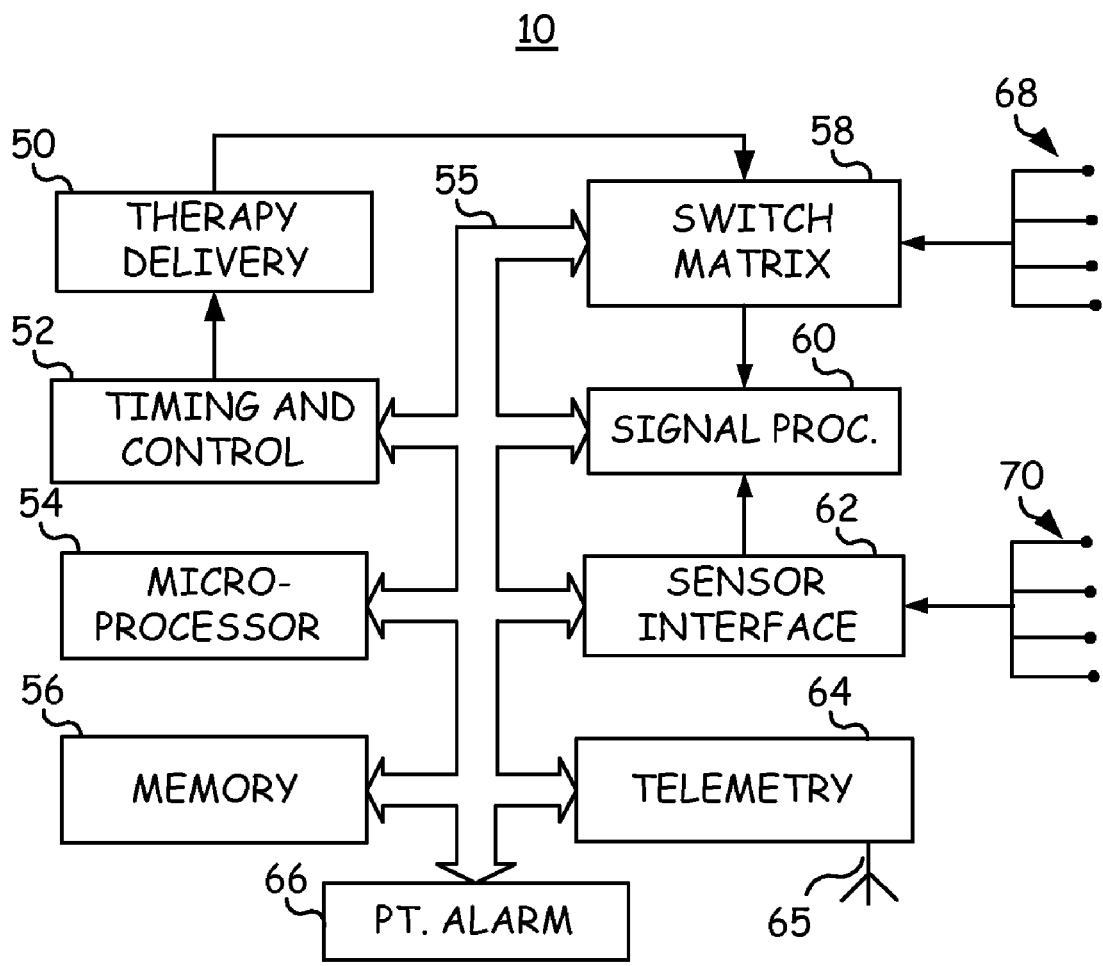
FIG. 2 is a block diagram of the IMD 10 shown in FIG. 1.

FIG. 2 is a block diagram of typical functional components of an IMD, such as IMD 10 shown in FIG. 1. IMD 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may be lead-based electrodes, leadless electrodes incorporated on IMD 10, and/or the IMD housing configured for use as a can or case electrode. Electrodes 68 may also be used for sensing electrical signals within the body, such as cardiac signals, or for measuring impedance, such as thoracic impedance for fluid monitoring as described above. Cardiac electrical signals are sensed using any of electrodes 68 for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias. Electrodes 68 may be used for measuring impedance signals for monitoring edema, respiration or heart chamber volume. Any of these signals may be used to detect a change indicating a worsening pathologic condition, which may trigger a patient alarm. Impedance signals can also be used for monitoring lead performance and detecting lead-related problems.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological events or changes in monitored physiological conditions may be defined as triggering conditions for a patient alarm to be generated by IMD 10.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Memory 56 is used to store operating commands and data for controlling device operation and for later retrieval to diagnose device function or patient condition. In accordance with the various embodiments of the present invention, parameter values or thresholds defining one or more patient alarm conditions may be stored in memory 56 and used by microprocessor 54 in triggering a patient alarm.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit. IMD telemetry circuitry 64 is used for receiving an externally generated event signal, for example from programmer 26 or home monitor 20 (shown in FIG. 1) for use by IMD 10 in determining a patient alarm threshold for a monitored physiological parameter.

In some embodiments, telemetry circuitry may require patient intervention to initiate or enable transfer/receipt of data to/from an external device. For example, telemetry circuitry 64 may require the use of an external programming head containing an external antenna to be positioned over IMD 10 as generally disclosed in U.S. Pat. No. 5,354,319 issued to Wyborny et al. Telemetry circuitry 64 may require manual "waking up" by the patient to enable data transmission or may require the patient to be within a limited communication range from the external device. In other embodiments, long range telemetry systems may be used allowing data to be transferred between IMD 10 and an external device automatically without intervention by the patient or another operator. Long-range telemetry systems are generally disclosed in U.S. Pat. No. 6,482,154 issued to Haubrich et al., incorporated herein by reference in its entirety.

IMD 10 may be equipped with patient alarm circuitry 66 for generating audible tones, a perceptible vibration, muscle stimulation or other sensory stimulation for notifying the patient that an alarm condition has been detected by IMD 10. Alternatively, a patient alarm may be provided by home monitor 20 in response to a signal received from IMD 10 as described previously.

Figure 3:
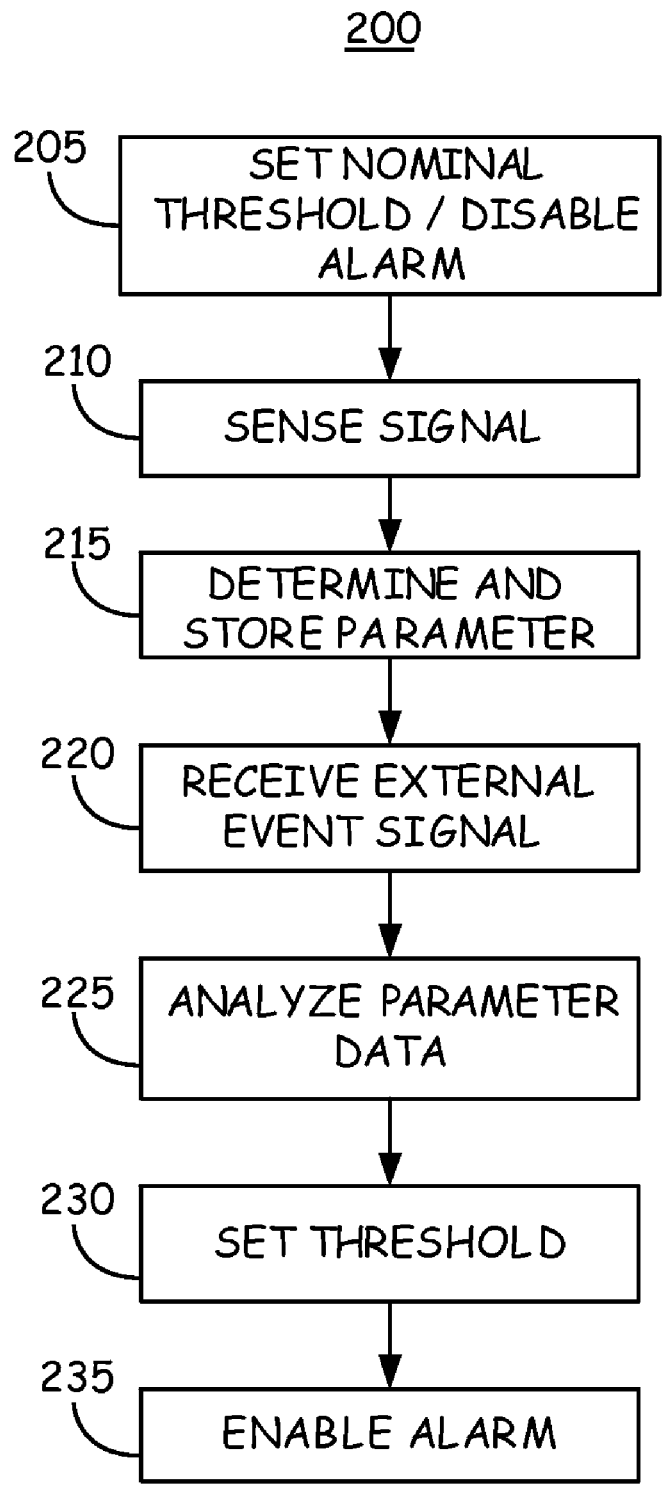
FIG. 3 is a flow chart of a method for automatically setting a patient alarm threshold according to one embodiment of the invention.

FIG. 3 is a flow chart 200 of a method for automatically setting a patient alarm threshold according to one embodiment of the invention. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 205, a patient alarm may be disabled to prevent delivery of false alarms until an appropriate threshold has been determined for the individual patient. Alternatively, a nominal threshold may be set for triggering a patient alarm in response to detecting a physiological event. A physician may initially select a very high threshold (or low threshold depending on the particular application) to prevent false alarms but still provide an alarm in response to a significantly worsening condition.

At block 210, one or more physiological signals are sensed by the IMD for use in detecting a physiological condition or event. In one embodiment, an thoracic impedance signal is sensed for monitoring pulmonary congestion. An amplified, filtered signal may be used directly for detecting a physiological event. Alternatively, the sensed signal may be analyzed for determining a physiological parameter. For example, an average, peak, slope or other feature of a sensed signal may be determined. As will be described briefly below, an impedance signal may be used for calculating a daily mean impedance for use in monitoring fluid levels in a patient. One or more parameters determined from one or more sensed physiological signal(s) is stored in IMD memory at block 215.

Physiological parameter data may be stored at block 215 until an external event signal is received at block 220. Alternatively, physiological parameter data may be stored in a looping, first in first out manner such that data is stored for a period of time until being replaced by newer data. Stored data may be compressed or transferred to an external device or central database if allocated memory is becoming low.

An external event signal is received at block 220 by the IMD via a communication link with an external device, such as a home monitor or programmer. As used herein, an external event signal refers generally to a signal received by the IMD corresponding to a clinical event or physiological condition detected by another device or person and communicated to the IMD via a telemetry link. A caregiver or a patient may use an external device (such as a home monitor or programmer) to indicate the occurrence of an adverse event that relates to a worsening condition of the patient that is correlated to a parameter being monitored by the IMD. In one embodiment, a parameter monitored by the IMD is correlated to thoracic congestion, and the external event signal received at block 220 corresponds to a hospitalization for symptoms relating to edema or heart failure. It is contemplated that in alternative embodiments, an IMD may receive an external event signal from another implanted device configured to monitor for an event resulting from a worsening condition monitored by the IMD.

Upon receiving the external event signal, the IMD analyzes the parameter data stored prior to the event for determining a patient alarm threshold. In some embodiments, the stored parameter data may have been transferred to an external device or central database during a routine data retrieval session. Such data may be retrieved by the IMD for use in determining a patient alarm threshold. Alternatively, the event signal may be received by the external device or central database which then performs the automatic threshold determination using data already retrieved from the IMD. A threshold determined by an external device or database may then be transmitted back to the IMD.

The patient alarm threshold is determined as function of the stored parameter data. The threshold may be determined as a mean or average parameter value occurring over a pre-determined period of time immediately prior to the event signal. For example, the IMD may compute a patient alarm threshold relating to pulmonary congestion as an average thoracic impedance parameter computed over a 72 hour period ending immediately prior to a hospitalization. Alternatively, the IMD may compute an average or mean parameter value over a time interval ending at a predetermined time prior to notification of the event. For example, the IMD may determine an average or mean parameter value occurring over a 24 hour period ending 72 hours prior to the event. In still another embodiment, the IMD may determine a parameter value at a predetermined time point prior to the event. For example, the IMD may determine a parameter value at a time point 72 hours prior to the event and store that value as the patient alarm threshold. The method for determining a patient alarm threshold and the particular time intervals used relative to receipt of an event signal will vary between embodiments depending on the particular parameter being monitored and corresponding event.

The newly computed threshold based on the analysis of the parameter data occurring prior to the external event signal is stored as the patient alarm threshold at block 230. The patient alarm is enabled at block 235. As such, an individualized alarm threshold is determined according to a patient's physiological condition. Typically the event signal received by the IMD is a serious clinical event associated with a worsening of the monitored parameter. The alarm threshold is determined using parameter values prior to the serious clinical event such that the alarm will precede such future clinical events, allowing a clinician and/or the patient to take actions toward preventing such events from occurring.

Figure 4:
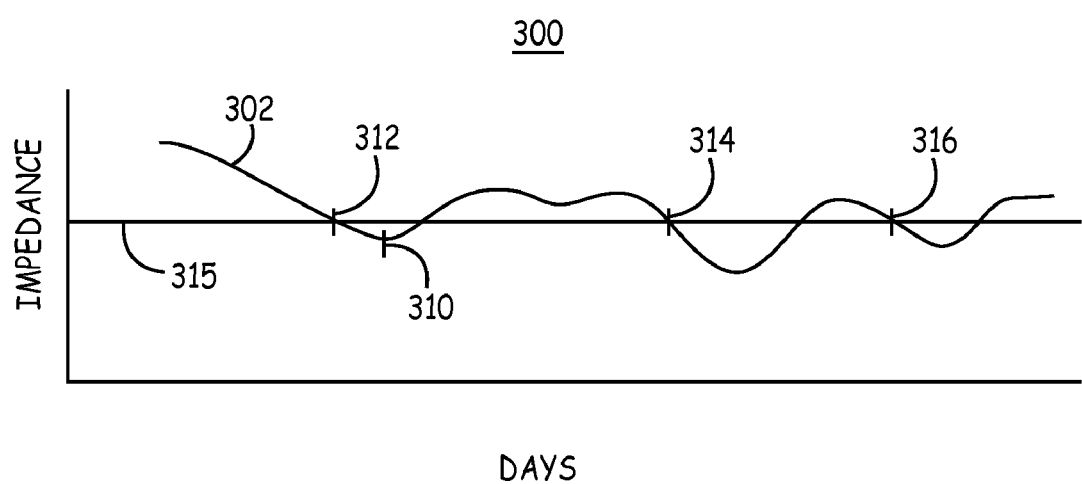
FIG. 4 is a timeline of impedance parameter data illustrating one method for determining a patient alarm threshold used for alerting the patient to increasing pulmonary congestion.

FIG. 4 is a timeline 300 of impedance parameter data illustrating one method for determining a patient alarm threshold for alerting the patient to increasing pulmonary congestion. Numerous algorithms may be employed for monitoring thoracic fluid level using impedance measurements. In one embodiment, period thoracic impedance measurements are employed for determining a daily mean impedance 302. At time point 310, a hospitalization takes place, and a clinician, using a programmer, sends a signal to the IMD indicating the hospitalization. The IMD responds to the event signal by determining an alarm threshold 315 using the daily mean impedance data. In one embodiment, the IMD determines the daily mean impedance at a predetermined time point 312 prior to the hospitalization 310. For example, the daily mean impedance at a predetermined time point 312 corresponding to 3 days prior to the hospitalization may be used to set alarm threshold 315. Subsequent threshold crossings of the daily mean impedance 302 occurring at time points 314 and 316 will trigger the delivery of a patient alarm.

It is recognized that various embodiments may include multiple sensor signals, multiple parameters, and/or use more complex mathematical or statistical relationships for computing a threshold. Furthermore, it is recognized that in other embodiments, a threshold determined in response to receiving an event signal may be used for triggering other device functions. For example, in some embodiments, the threshold may be used to trigger delivery or adjustment of a therapy. Furthermore, it is recognized that multiple thresholds may be determined in response to an event signal corresponding to more than one monitored parameter and/or for triggering more than one device function. The methods for computing the threshold will take into account the desired warning time that a patient/clinician will have prior to manifestation of a serious clinical event. By triggering the patient alarm and/or other device functions in advance of the serious event, the event may be prevented or at least lessened in severity.

Thus, an implantable medical device system and associated methods have been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
a sensor for sensing a first signal in a patient;
detection circuitry for receiving the first signal and determining a parameter corresponding to the first signal;
memory for storing the parameter; and
control circuitry configured to receive a second signal corresponding to a defined first event following storage of the parameter and further configured to determine a threshold from the stored parameter in response to receiving the second signal;
wherein the detection circuitry comprises circuitry for detecting a defined second event in response to the parameter subsequently crossing the determined threshold; and
wherein determining the threshold comprises determining the threshold using a value of the parameter stored at a time prior to the receipt of the second signal.

2. A device according to claim 1, further comprising alarm circuitry for generating an alarm signal in response to the detected second event.

3. An implantable medical device, comprising:
a sensor for sensing a first signal in a patient;
detection circuitry for receiving the first signal and determining a parameter corresponding to the first signal;
memory for storing the parameter; and
control circuitry configured to receive a second signal corresponding to a defined first event following storage of the parameter and further configured to determine a threshold from the stored parameter in response to receiving the second signal;
wherein the detection circuitry comprises circuitry for detecting a defined second event in response to the parameter subsequently crossing the determined threshold; and
further comprising telemetry circuitry coupled to the control circuitry and wherein the second signal comprises an externally generated signal received by the telemetry circuitry.

4. A device according to claim 3 further comprising alarm circuitry for generating an alarm signal in response to the detected second event.

5. An implantable medical device, comprising:
a sensor for sensing a first signal in a patient;
detection circuitry for receiving the first signal and determining a parameter corresponding to the first signal;
memory for storing the parameter; and
control circuitry configured to receive a second signal corresponding to a defined first event following storage of the parameter and further configured to determine a threshold from the stored parameter in response to receiving the second signal;
wherein the detection circuitry comprises circuitry for detecting a defined second event in response to the parameter subsequently crossing the determined threshold; and
wherein the second signal corresponds to a worsening of the parameter subsequent to a storage of the parameter.

6. A device according to claim 5 further comprising alarm circuitry for generating an alarm signal in response to the detected second event.

7. An implantable medical device, comprising:
a sensor for sensing a first signal in a patient;
detection circuitry for receiving the first signal and determining a parameter corresponding to the first signal;
memory for storing the parameter; and
control circuitry configured to receive a second signal corresponding to a defined first event following storage of the parameter and further configured to determine a threshold from the stored parameter in response to receiving the second signal;
wherein the detection circuitry comprises circuitry for detecting a defined second event in response to the parameter subsequently crossing the determined threshold; and
wherein the sensor comprises an impedance sensor.

8. A device according to claim 7 wherein the impedance sensor is configured for sensing thoracic impedance.

9. A device according to claim 7 further comprising alarm circuitry for generating an alarm signal in response to the detected second event.

10. An implantable medical device system, comprising:
an implanted sensor for sensing a first signal in a patient;
detection circuitry for receiving the first signal and determining a parameter corresponding to the first signal;
memory for storing the parameter;
control circuitry configured to receive a second signal corresponding to a defined first event following storage of the parameter and further configured to determine a threshold from the stored parameter in response to receiving the second signal;
an implantable telemetry circuit providing the second signal to the control circuit; and
an external telemetry circuit in bidirectional communication with the implantable telemetry circuit, the external telemetry circuit adapted to transmit the second signal to the implantable telemetry circuit;
wherein the detection circuitry comprises circuitry for detecting a defined second event in response to the parameter subsequently crossing the determined threshold.

11. A system according to claim 10 further comprising alarm circuitry for generating an alarm signal in response to the detected second event.

12. A system according to claim 10 wherein determining the threshold comprises determining a threshold based upon a value of the parameter stored at a time prior to the receipt of the second signal.

13. A system according to claim 10 wherein the sensor comprises an impedance sensor.

14. A system according to claim 13 wherein the impedance sensor is configured for sensing thoracic impedance.

* * * * *